(12) United States Patent
Urey et al.

(10) Patent No.: US 10,739,670 B2
(45) Date of Patent: Aug. 11, 2020

(54) PHYSICAL OBJECT RECONSTRUCTION THROUGH A PROJECTION DISPLAY SYSTEM

(71) Applicant: KOC Universitesi, Istanbul (TR)

(72) Inventors: Hakan Urey, Istanbul (TR); Shoaib Soomro, Istanbul (TR)

(73) Assignee: Augmency Teknoloji Sanayi Anonim Sirketi, Istanbul (TR)

( * ) Notice: Subject to any disclaimer, the term of this patent is extended or adjusted under 35 U.S.C. 154(b) by 0 days.

(21) Appl. No.: 15/780,763

(22) PCT Filed: Dec. 4, 2015

(86) PCT No.: PCT/TR2015/050227
§ 371 (c)(1),
(2) Date: Jun. 1, 2018

(87) PCT Pub. No.: WO2017/095341
PCT Pub. Date: Jun. 8, 2017

(65) Prior Publication Data
US 2019/0086787 A1    Mar. 21, 2019

(51) Int. Cl.
*G03B 21/625* (2014.01)
*A61B 34/00* (2016.01)
(Continued)

(52) U.S. Cl.
CPC ............ *G03B 21/625* (2013.01); *A61B 34/25* (2016.02); *A61B 90/37* (2016.02); *G02B 5/136* (2013.01); *G02B 27/0093* (2013.01); *G02B 27/0101* (2013.01); *G02B 27/017* (2013.01); *G02B 27/0179* (2013.01); *G03B 21/58* (2013.01); *G03B 21/62* (2013.01); *G06F 3/014* (2013.01);
(Continued)

(58) Field of Classification Search
None
See application file for complete search history.

(56) References Cited

U.S. PATENT DOCUMENTS

2001/0010555 A1    8/2001    Driscoll, Jr.
2002/0067466 A1    6/2002    Covannon et al.
(Continued)

OTHER PUBLICATIONS

International Search Report and Written Opinion, dated Sep. 20, 2016, pp. 1-10, issued in International Application No. PCT/TR2015/050227, European Patent Office, Rijswijk, The Netherlands.
International Preliminary Report on Patentability, dated Jun. 5, 2018, pp. 1-8, issued in International Application No. PCT/TR2015/050227, European Patent Office, Munich, Germany.

*Primary Examiner* — Hung Q Dang
(74) *Attorney, Agent, or Firm* — Brinks Gilson & Lione

(57) ABSTRACT

A projection display system may be used to display projected images on an image display layer embedded on the surface of an object. The projection display system may include an image capturing device, a projector unit and a passive screen. The passive screen may include a display layer effecting display of at least one image projected thereon. The passive screen is further placeable on a surface of an object in the manner that said image capturing device in optical communication with said passive screen identifies physical boundaries of said passive screen and the projector unit projects at least one image scaled onto the passive screen within the boundaries thereof.

20 Claims, 13 Drawing Sheets

(51) Int. Cl.
 *G03B 21/62* (2014.01)
 *G02B 27/01* (2006.01)
 *G02B 27/00* (2006.01)
 *G03B 21/58* (2014.01)
 *G06T 7/13* (2017.01)
 *G06T 7/521* (2017.01)
 *G06F 3/01* (2006.01)
 *H04N 9/31* (2006.01)
 *A61B 90/00* (2016.01)
 *G02B 5/136* (2006.01)
 *G06F 3/042* (2006.01)
 *G06T 7/70* (2017.01)

(52) U.S. Cl.
 CPC .............. *G06T 7/13* (2017.01); *G06T 7/521* (2017.01); *H04N 9/3173* (2013.01); *H04N 9/3188* (2013.01); *A61B 2090/366* (2016.02); *G02B 2027/013* (2013.01); *G02B 2027/014* (2013.01); *G02B 2027/0138* (2013.01); *G02B 2027/0187* (2013.01); *G06F 3/016* (2013.01); *G06F 3/0425* (2013.01); *G06T 7/70* (2017.01); *G06T 2207/10048* (2013.01)

(56) References Cited

U.S. PATENT DOCUMENTS

| | | |
|---|---|---|
| 2003/0156187 A1 | 8/2003 | Gluckman et al. |
| 2004/0042000 A1* | 3/2004 | Mehrl ................. G01M 11/005 356/218 |
| 2008/0204663 A1* | 8/2008 | Balogh ................ H04N 13/363 353/10 |
| 2010/0315491 A1* | 12/2010 | Carter .................... G03B 15/10 348/51 |
| 2011/0053688 A1* | 3/2011 | Crawford ................ A63D 5/04 463/31 |
| 2011/0096183 A1* | 4/2011 | Robertson .............. H04N 5/275 348/222.1 |
| 2012/0076353 A1 | 3/2012 | Large |
| 2013/0038696 A1 | 2/2013 | Ding et al. |
| 2013/0300637 A1 | 11/2013 | Smits et al. |
| 2014/0160115 A1* | 6/2014 | Keitler ................... G01B 11/00 345/419 |
| 2015/0138349 A1* | 5/2015 | Hebert .................. G01B 11/25 348/136 |
| 2015/0234221 A1* | 8/2015 | Anderson ........... G02F 1/13363 349/113 |

\* cited by examiner

PHYSICAL OBJECT RECONSTRUCTION THROUGH A PROJECTION DISPLAY SYSTEM

RELATED APPLICATIONS

The present patent document is a 371 of PCT Application Serial No. PCT/TR2015/050227, filed Dec. 4, 2015, designating the United States and published in English, which is hereby incorporated by reference.

BACKGROUND

1. Technical Field

The present disclosure relates to a system in the form of a projection display system intended to be used to display projected images on an image display layer embedded on the surface of an object.

2. Background

The concept of combination of a multitude of singular views of a real object so as to be processed by a processing unit, by which an image of the object with enhanced visual properties is obtainable, is subject to a wide range of applications in the state of the art.

BRIEF SUMMARY

As a basic example, a certain object with a certain physical complexity can be digitally reconstructed to selectively exhibit different physical properties such as for instance its coloring, by way of making use of and by processing captured images thereof. It is to be noted that reconstructing 3D views of a certain object may require substantial image processing and is therefore computationally intensive. On the other hand, digital reconstruction of a physical object inherently lacks the most apparent visual advantages for viewers if the physical object itself is not used as a base model in the physical world for reconstruction; or in other words, if the reconstruction is not carried out directly on the surface of the base model itself.

One of the prior art publications in the technical field may be referred to as US 20130038696, which teaches the ray modeling of multi-view/light-field imaging with single camera and curved mirror array. More particularly, US 20130038696 discloses a system in which a catadioptric camera creates images from a 3D scene by creating ray images defined as 2D arrays of ray-structure picture-elements (ray-xels). Each ray-xel captures light intensity, mirror-reflection location, and mirror-incident light ray direction. A 3D image is then rendered from the ray images by combining the corresponding ray-xels. The catadioptric camera system of US 20130038696 involves a multiplicity of curved mirrors arranged into a mirror array for reflecting a desired 3D scene and a digital imaging system capturing ray images of said curved mirrors, each of said ray images being a two-dimensional array of ray-structure picture-elements (ray-xels). US 20130038696 provides that each respective ray-xel includes a light intensity measure according to a predefined color model, mirror-reflection location coordinates, and mirror-incident ray direction coordinates. Another prior art publication in the technical field may be referred to as US 2003156187, which discloses catadioptric sensors using one or more planar mirrors to produce rectified stereoscopic images using only one image detector. By combining multiple views using the mirrors, a composite stereo image that is rectified is formed. The document also teaches different configurations of mirrors to generate virtual camera viewpoints.

A further prior art publication in the present technical field is US 2001010555, disclosing a panoramic camera apparatus in the form of a catadioptric camera for wide angle imaging capturing a 360 degree panoramic image. The document describes use of a single camera with spherical or parabolic mirrors.

It is to be noted that defining physical boundaries of a certain object so as to allow reconstruction of the specified object by way of projecting a plurality of images thereon provides a much more realistic reconstruction of the physical object in the manner that its appearance can be selectively changed according to a predetermined set of physical criteria or conditions. According to an embodiment of the projection display system disclosed herein, a display layer embedded on the surface of a certain object effective in displaying a projected image so as to demonstrate a selectively reconstructed form of said object is provided.

According to an embodiment of the projection display system, a head-mounted projection assembly combined with a camera system cooperatively interacts with the specific object to which selectively configured reconstruction is applied.

An aspect of the projection display system is to provide a virtual object reconstruction system by means of a display layer embeddable on a physical object to display projected content in a selectively changed manner.

Another aspect of the projection display system is to provide a wearable system involving a head-mounted projection assembly combined with a camera system.

A further aspect of the projection display system is to provide a passive transparent retroreflective (TRR) high gain screen directly applicable on an object intended to be reconstructed.

BRIEF DESCRIPTION OF THE FIGURES

Accompanying drawings are given solely for the purpose of exemplifying an object reconstruction system, whose advantages over prior art were outlined above and will be explained in brief hereinafter.

The drawings are not meant to delimit the scope of protection nor should they be referred to alone in an effort to interpret the scope without recourse to the technical disclosure herein.

DETAILED DESCRIPTION OF THE DRAWINGS AND THE PRESENTLY PREFERRED EMBODIMENTS

Figure 1:
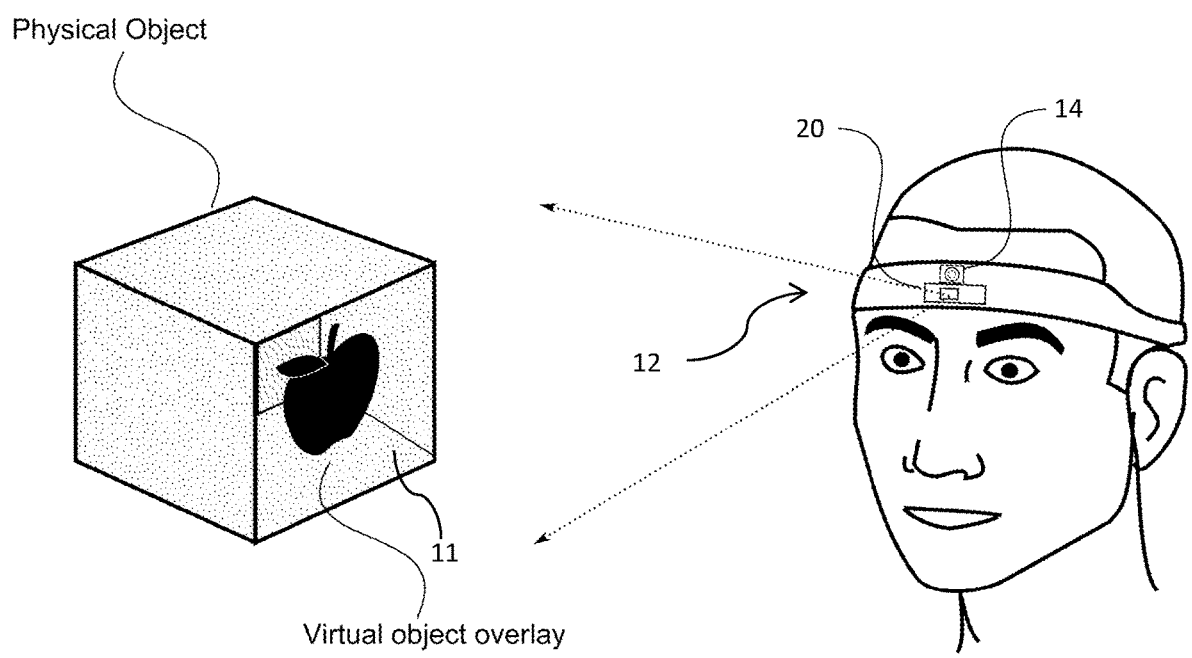
FIG. 1 demonstrates the application of a head-mountable device comprising a projector unit and an image capturing device with a passive screen in the form of a semi-transparent retroreflective screen. A physical object is covered with the passive screen and the head-mountable device performs real-time perspective capture, projection mapping and display on object surface.
Figure 2:
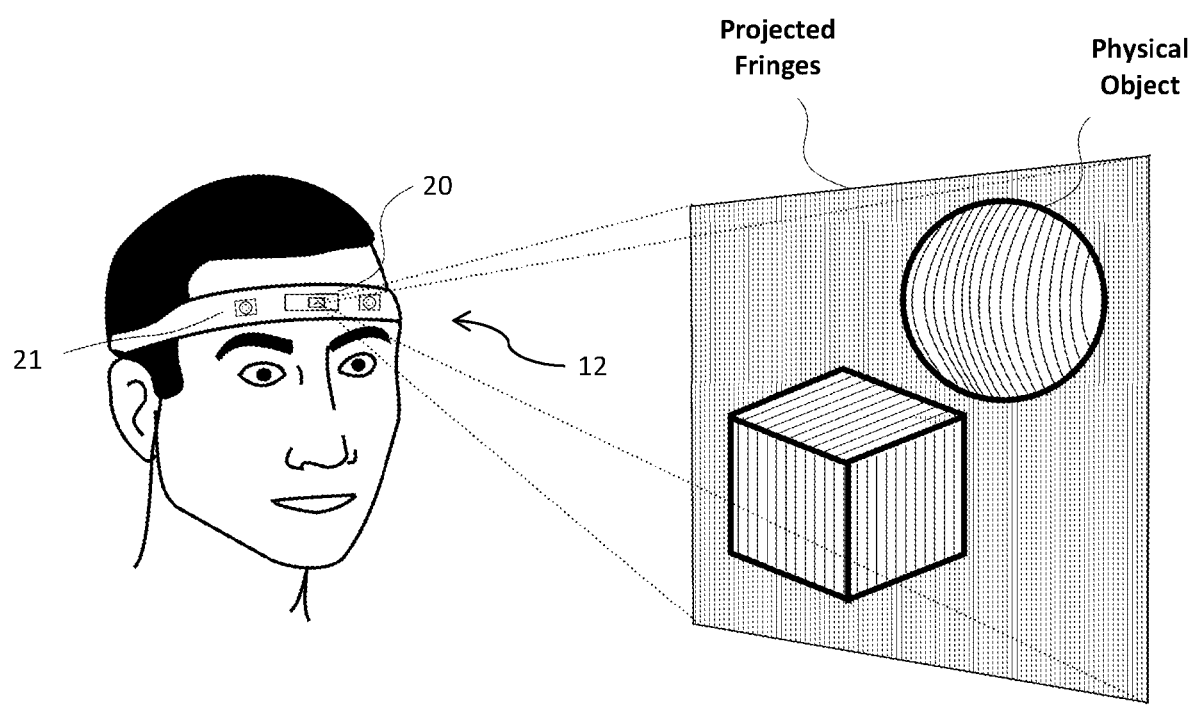
FIG. 2 demonstrates working mechanism of depth sensing with a head-mountable device using structured light by the projector unit according to an embodiment. An auxiliary camera in the form of an IR or near IR camera integrated into the head-mountable device captures the projected fringe patterns by the projector unit with IR or near IR laser based fringe projection.

The following numerals are referred to herein:
11) Passive screen
12) Head-mountable device
13) Screen substrate
14) Image capturing device
15) Retroreflective cell
16) Vertical diffusive cell
17) Cylindrical lens micro-strip
18) Reflective coating
19) Cylindrical lens
20) Projector unit
21) Auxiliary camera
22) Hand-wearable screen unit
23) Retroreflective layer
24) Semi-transparent vertical diffusive layer A system in the form of a projection display system is proposed. An image capturing device (14) is provided in the form of a single high-resolution camera optically communicating with a passive screen (11) in the manner that the image capturing device (14) defines physical boundaries of said passive screen (11) embedded on the surface of a certain object so as to allow reconstruction of the specified object by way of projecting a plurality of images thereon. A projector unit (20) projects images on the passive screen (11) in optical communication therewith. In other words, image capturing is effectuated by the high-resolution camera while projection is effected by the projector unit (20) and the passive screen (11) covering the surface of the object assumes the role of displaying the projected images. The passive screen (11) preferably comprises a screen substrate (13). The optical interaction of the image capturing device (14), i.e. the high-resolution camera, and the projector unit (20) with the passive screen (11) can be realized in different positionment setups relative to the passive screen (11). The passive screen (11) is a polymer-based flexible and thereby substantially restructurable medium placeable on an object to be visually reconstructed while the image capturing device (14) and the projector unit (20) can be incorporated into a head-mountable device (12). The head-mountable device (12) therefore comprising the image capturing device (14) and the projector unit (20) ensures that the image capturing device (14) can optically communicate with the passive screen (11) to effectively determine physical boundaries of the passive screen (11) and the projector unit (20) can project images to dynamically cover the calculated projection area by real-time boundary-based modifications within the boundaries of the passive screen (11) placed on the object.

Therefore, the image capturing device (14) operatively coupled to the projector unit (20) within the head-mountable device (12) performs real-time perspective capture and projection mapping by calculation of the exact location and extent of the passive screen (11) and adjustment of the scaling of the images to be projected to fit onto the object. Said projector unit (20) effectuates reconstruction of the object covered by the passive screen (11) through projection of predetermined images in a selective manner. Use of a head-mountable device (12) for both determining boundaries of the passive screen (11) and image projection advantageously eliminates scaling problems and provides real-time reconstruction of the object in view of the changing viewing angle of the user, i.e. when the user moves relative to the object, the object moves relative to the user or both move relative to each other. Alternatively, a fixed position image capturing device (14) together with a projector unit (20) can be used as a table-top device or a wall-mounted device.

The projector unit (20) is a high-resolution projector unit (20), typically in the form of a pico-projector preferably combined with the image capturing device (14) within the head-mountable device (12). The projector unit (20) projects an image on the passive screen (11) and the latter effects displaying of the projected images thereon as will be delineated hereinafter. The projector unit (20) is a laser scanning projector operated with battery. The passive screen (11) is structured in the form of a micro-patterned retroreflective surface. The passive screen (11) effectuates reflection of the projected images by means of a semi-transparent retroreflective layer (23). The passive screen (11) comprises retroreflective cells (15) in the form of retroreflective display patches. The passive screen (11) preferably comprises retroreflective cells (15) such that a semi-transparent screen layer having display cells of retroreflective microspheres (or microbeads) is obtained to provide retro-reflection. Alternatively, retroreflective cells (15) can be realized by using retroreflective paint so as to achieve the same retro-reflection effect. In a further alternative of the projection display system, the retro-reflection effect is achieved with paint mixed with retroreflective microspheres.

Retroreflective cells (15) are made of hemi-spherically coated glass microspheres spread over an adhesive layer of a screen substrate (13) in a randomly-oriented manner, the adhesive layer containing a pressure-sensitive or radiation curable (UV) adhesive/resin. Retro-reflection can be alternatively achieved through tightly placing transparent microspheres on a microspheres reflective coating as a thin (approximately 100 nm) metallic (preferably Aluminum) film and pressure sensitive adhesive/resin on the screen substrate (13).

Retro-reflection cone angle emanating from a single microsphere can be improved by using microspheres in a range of small (10 µm) to larger (100 µm) sizes to provide better viewing at eye position. The diameter of the microspheres is preferably in the range of 30 to 100 µm.

Further, the retroreflective cells (15) made of hemispherically coated randomly-oriented glass microspheres or of transparent microspheres placed on the microspheres reflective coating and adhesive layer have a certain size in the manner that the retroreflective cells (15) are made small enough not to be seen granular when viewed from a comfortable viewing distance (25 cm or higher). The retroreflective cells' (15) pitch can be smaller than 1 mm or even 250 µm so that it cannot be resolved by the eye. The retroreflective cells' (15) pattern preferably has a pitch period of 250 µm to 2 mm with a fill-factor of 10% to 50%.

The surface pattern of the retroreflective cells (15) of the passive screen (11) can have various configurations. The retroreflective cells (15) in the form of circular or square-shaped cell portions being evenly distributed as linearly aligned, hexagonally disposed or randomly distributed cells are possible. Therefore, while the shape of the retroreflective cells (15) can be circular or square/rectangular, the distribution pattern can be square, hexagonal, dithered or in the form of vertical/horizontal strips. Randomly-distributed patches are especially effective in eliminating Moire-pattern artifacts.

Figure 3A:
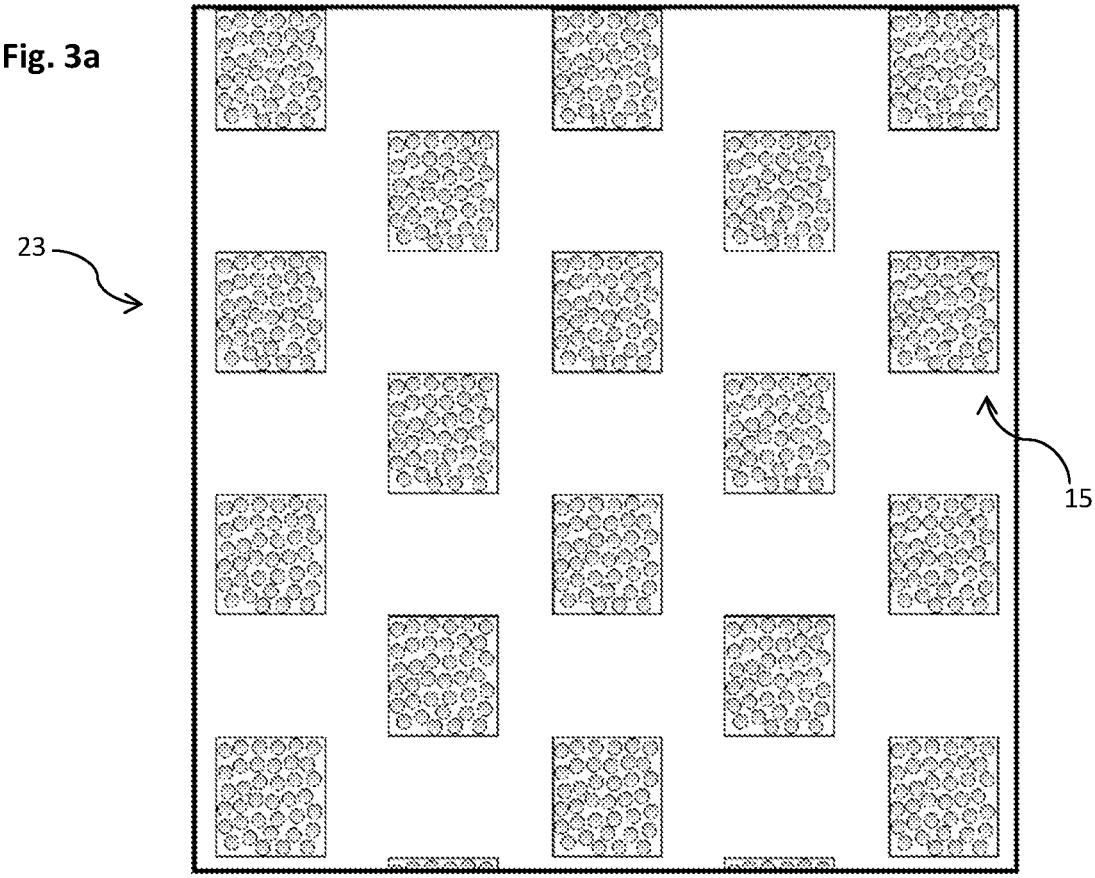
FIGS. 3a, 3b and 3c demonstrate the construction of a transparent passive screen with vertical viewing zone according to an embodiment. The passive screen consists of a semi-transparent retroreflective layer and a semi-transparent vertical diffusive layer. The semi-transparent retroreflective layer comprises retro-reflective microbeads (microspheres) in the form of micro-patches (cells) (FIG. 2a) and the semi-transparent vertical diffusive layer comprises micro-patches (cells) of cylindrical refractive lenses (FIG. 2b). The two layers are bonded with each other with said semi-transparent vertical diffusive layer being disposed on top (FIG. 3c), whereby a semi-transparent vertically diffused only screen is constructed.
Figure 3B:
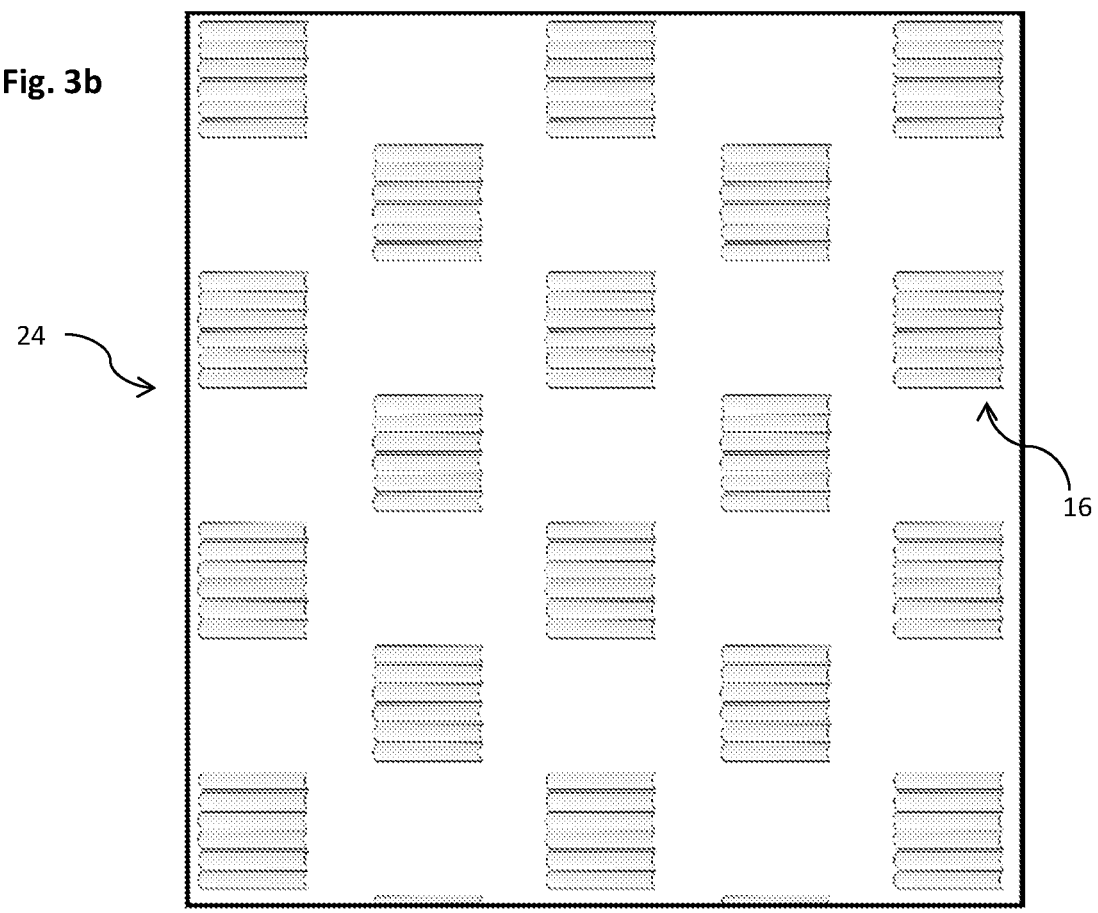
Figure 3C:
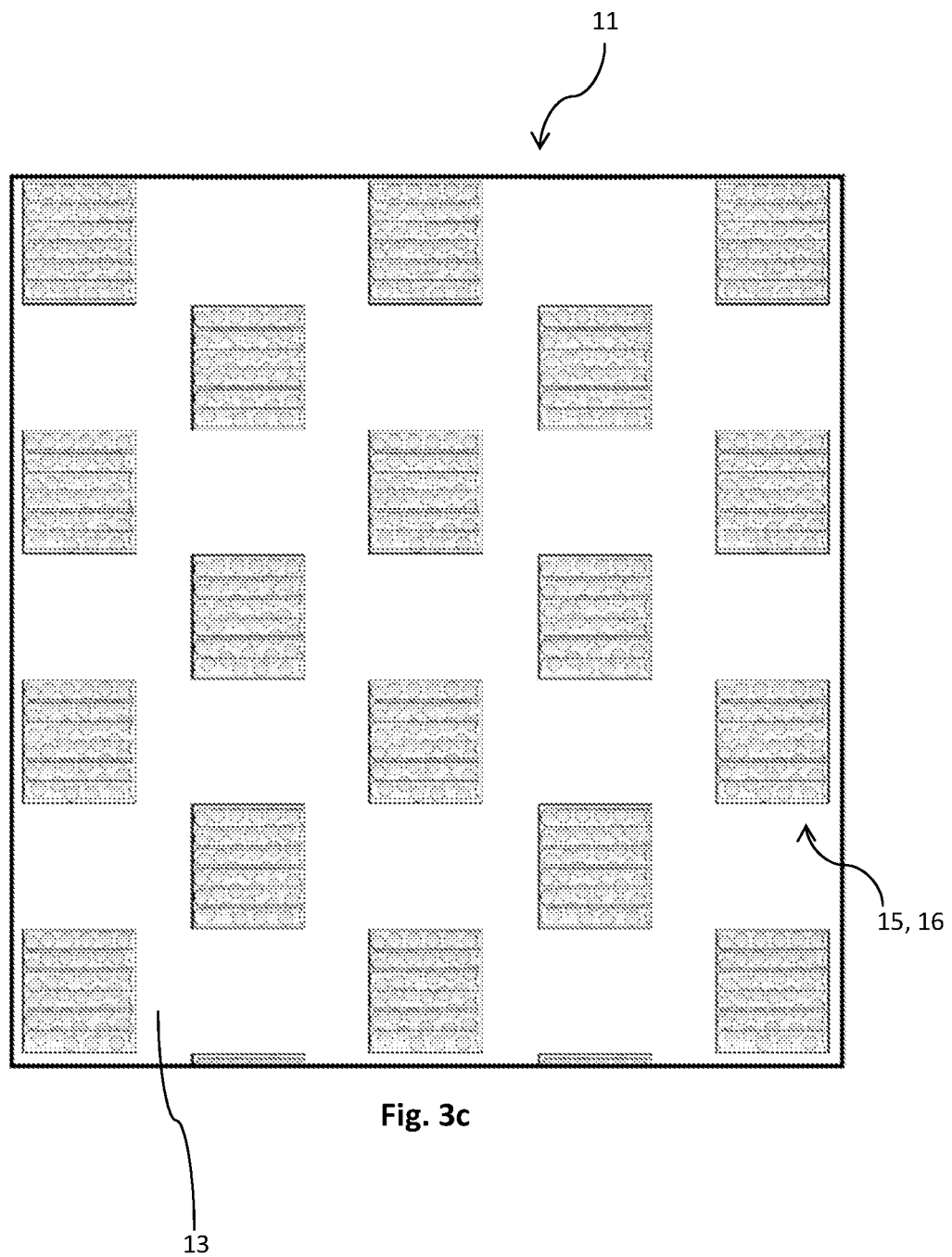
Figure 4:
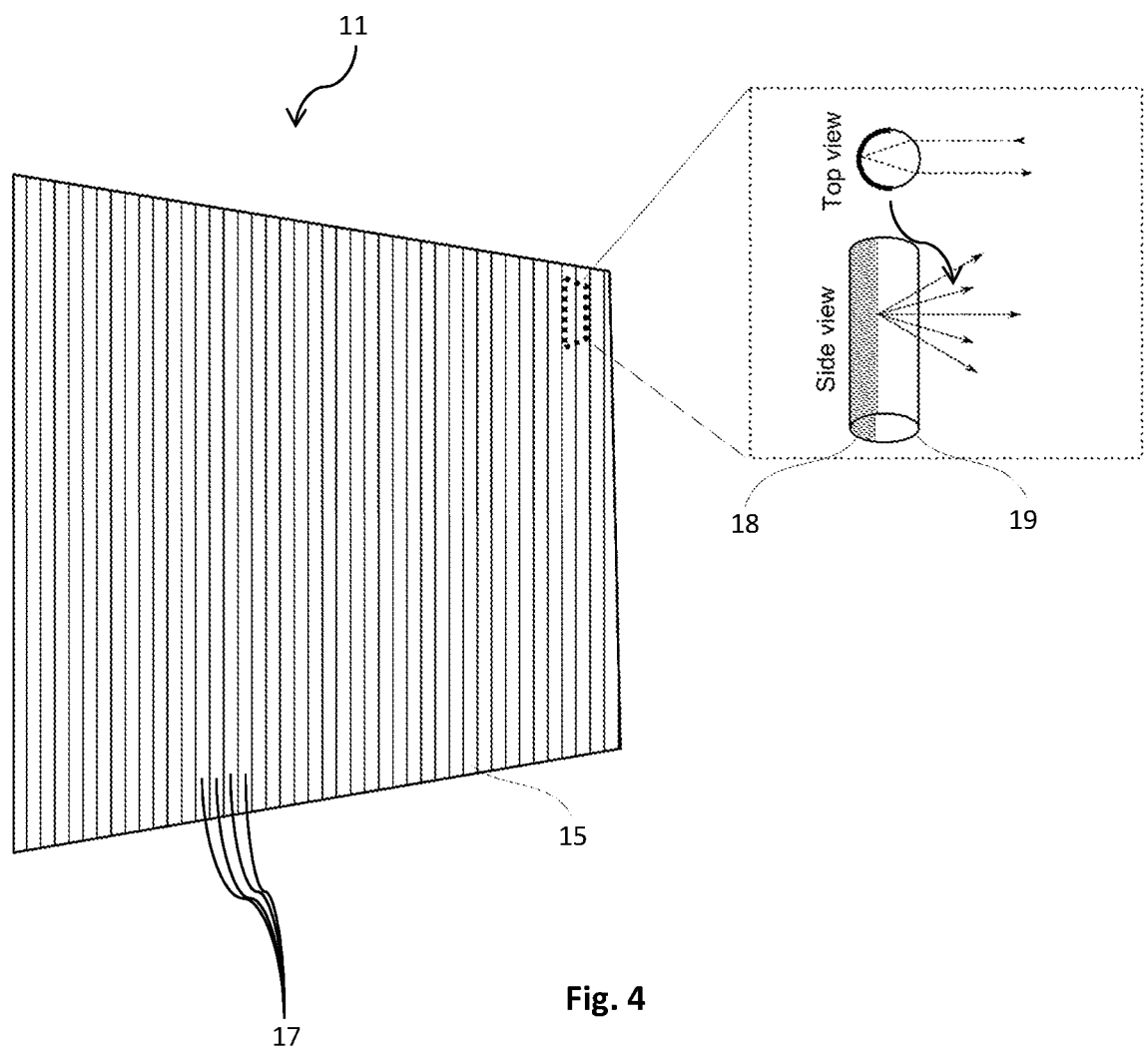
FIG. 4 demonstrates an alternative embodiment for creating a passive screen in the form of a vertically diffused only screen. The passive screen comprises perforated vertical micro strips of cylindrical. The cylindrical lenses are hemi-spherically coated with reflective material and each cylindrical lens retro-reflects light in one and scatters light in other direction, creating a screen with vertical or horizontal viewing zone only.

Alternatively, the passive screen (11) may have an additional layer in the form of a semi-transparent vertical diffusive layer (24), which is particularly advantageous in applications requiring vertical diffusion of the projected images. To this end, a semi-transparent retroreflective layer (23) and a semi-transparent vertical diffusive layer (24) as a separate layer being placed on top of the first layer together form the passive screen (11). The semi-transparent vertical diffusive layer (24) comprises micro-patches (cells) of cylindrical lenses as shown in FIG. 3b. The resulting passive screen (11) of FIG. 3c constructed by attaching the two layers is a semi-transparent vertically diffused only screen. An alternative embodiment, also allowing creation of a passive screen (11) in the form of a vertically diffused only screen is realized using perforated cylindrical lens micro strips (17) (in the form of fibers with n=2). The cylindrical lenses (19) in the micro-strips are hemi-spherically coated with reflective coating (18) material (aluminum, sliver, nickel). Each cylindrical lens (19) retro-reflects light in one direction (as shown in top view in FIG. 4) and scatters light in another direction (as also shown in side view in FIG. 4) creating a screen with a desired viewing zone only.

Figure 5:
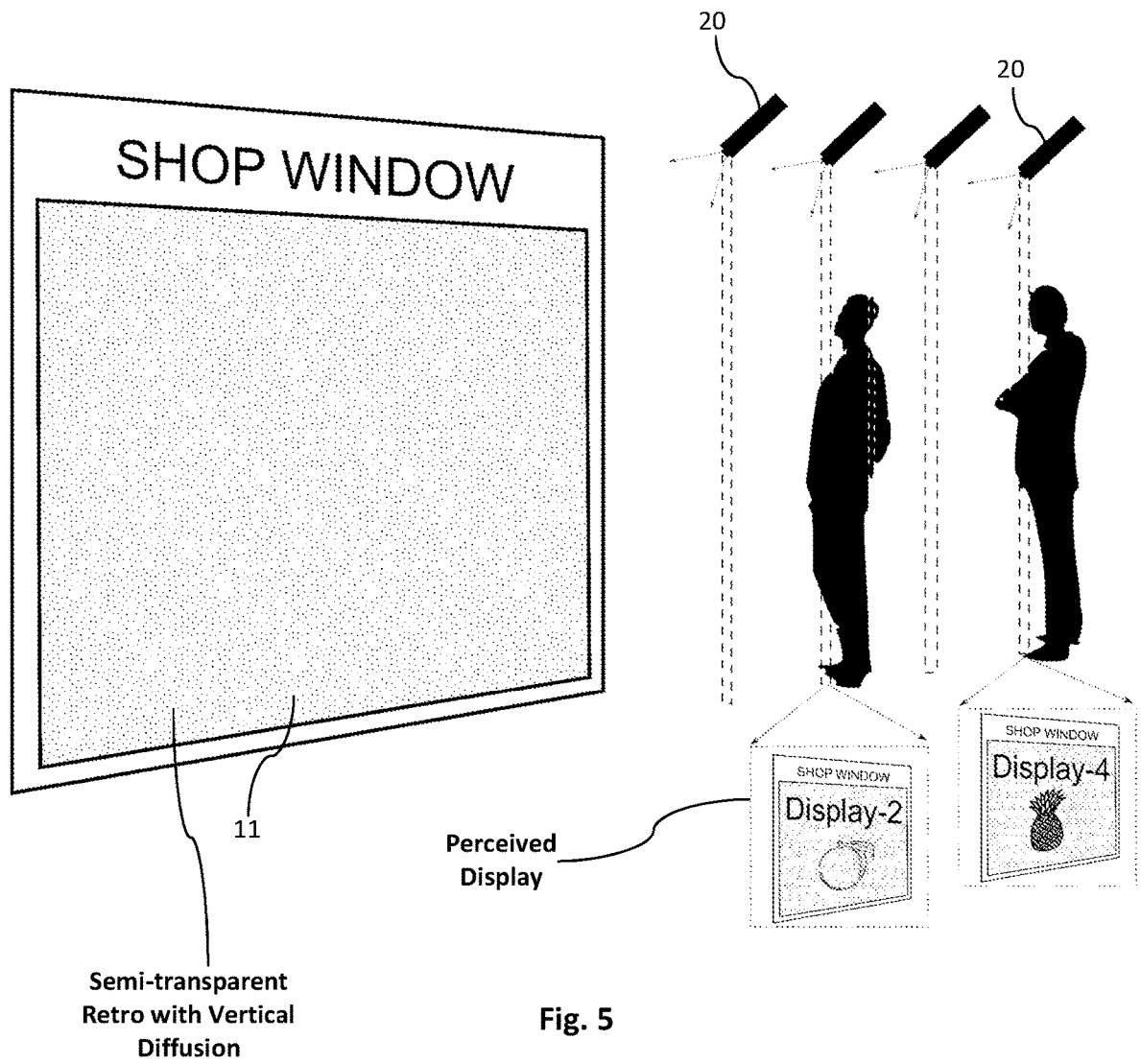
FIG. 5 demonstrates the application of a passive semi-transparent screen in the form of a vertically diffused retroreflective screen in glass window settings. A set of projector units are configured in the way to use the same passive screen to display independent contents with different viewing areas.

As shown in FIG. 5, a passive screen (11) in the form of a vertically diffused screen is advantageously usable in a shop window setup with a set of projector units (20). The passive screen (11) can be realized either by a semi-transparent retroreflective layer (23) together with a semi-transparent vertical diffusive layer (24) on top thereof as in FIG. 3c or by means of vertically extending cylindrical lens micro strips (17) as in FIG. 4. In FIG. 5's setup, the projector units (20) are disposed relative to the passive screen (11) so as to use the same passive screen (11) to display independent contents for different viewers with different viewing areas. Each projector unit (20) creates a vertical viewing zone (viewing slits) when the viewer's eyes are aligned with viewing slits of any projector unit (20). When viewers approach a shop's window passing by, they will see the specific display content on the same shared and transparent passive screen (11).

Figure 6:
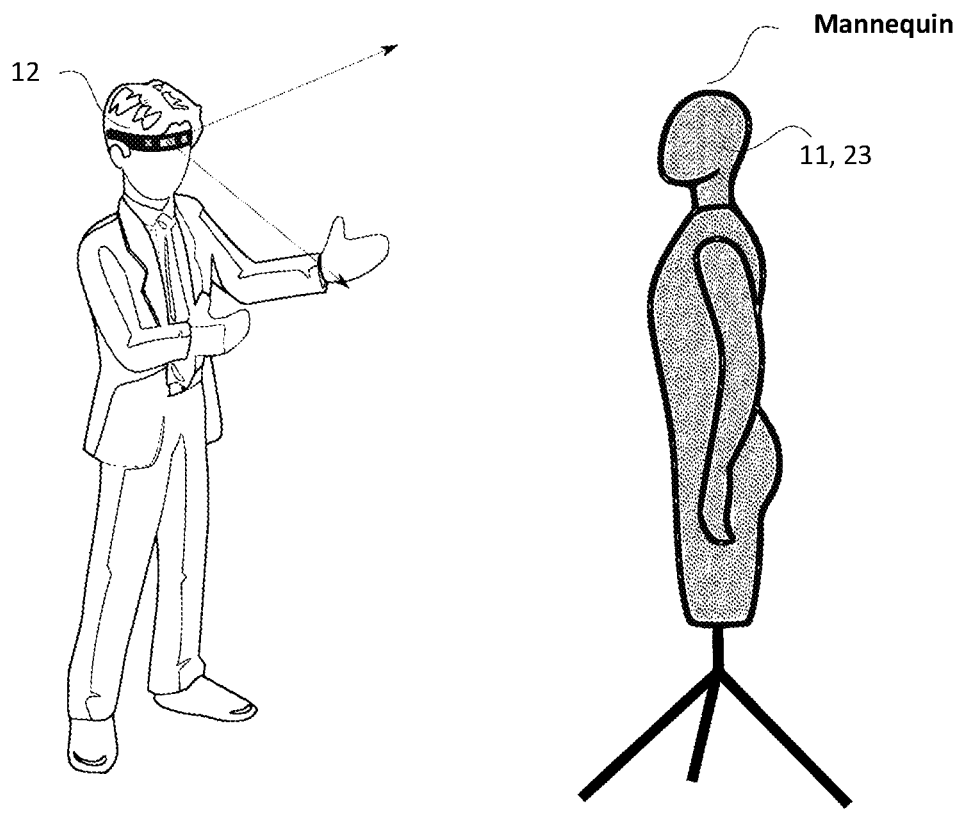
FIG. 6 demonstrates another use of the head mountable device, where a mannequin covered with a semi-transparent retroreflective surface is used to project virtual display content using said head mountable device. The same mannequin is also usable as shared display in multiuser settings.
Figure 7:
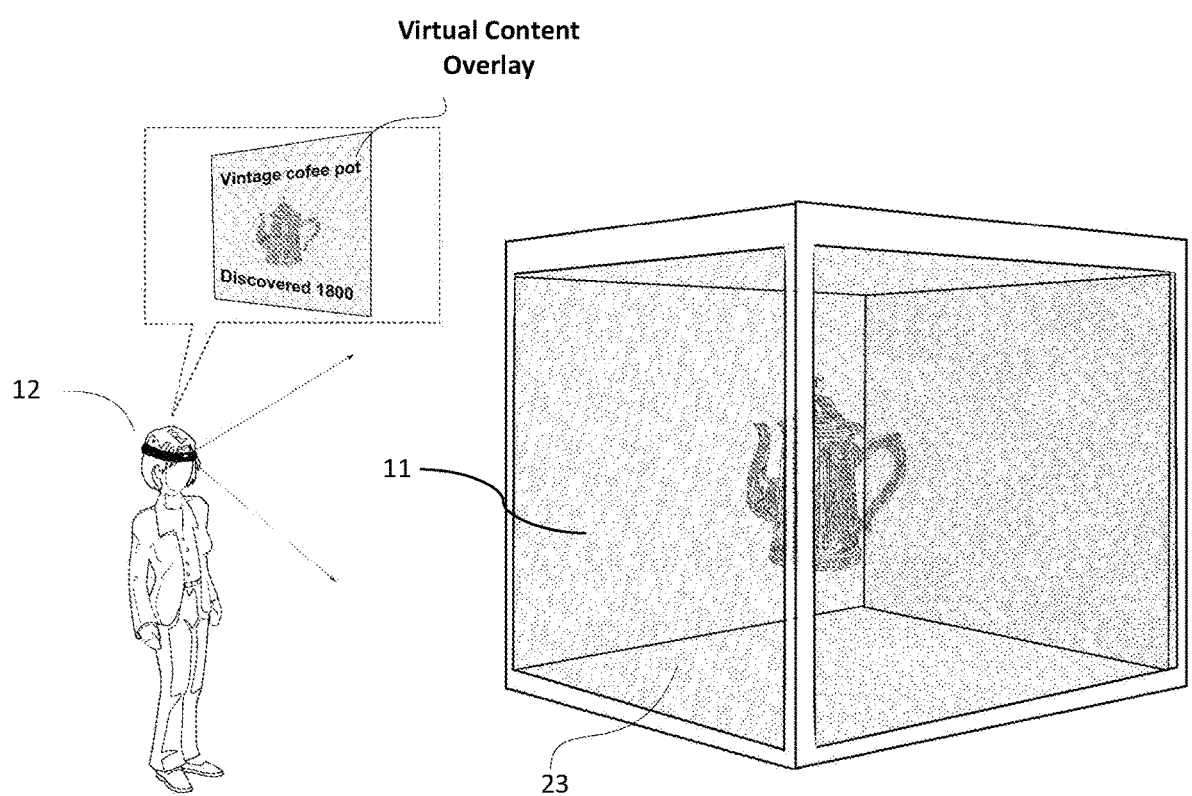
FIG. 7 demonstrates the use of the semi-transparent retroreflective layer in the museum settings, where protective glass walls of an exhibition area is covered with transparent retro-reflective surface and a head-mountable device comprising the projector unit and the image capturing device is used to project virtual content and all related information on the glass surface. The passive screen works as transparent glass for others but projection screen for a visitor wearing the head-mountable device.
Figure 8:
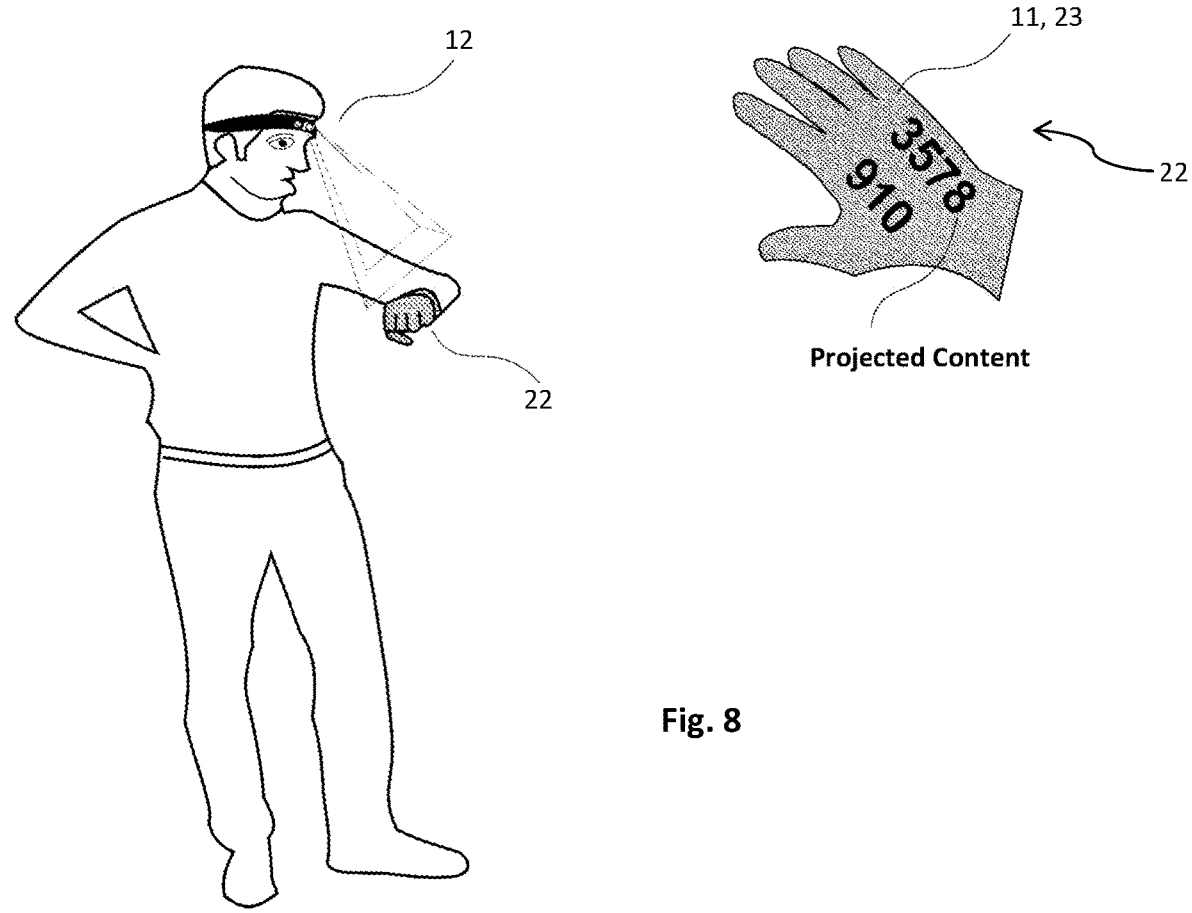
FIG. 8 demonstrates another application according to another embodiment where a hand-wearable screen unit is covered with a semi-transparent retro-reflective layer.
Figure 9:
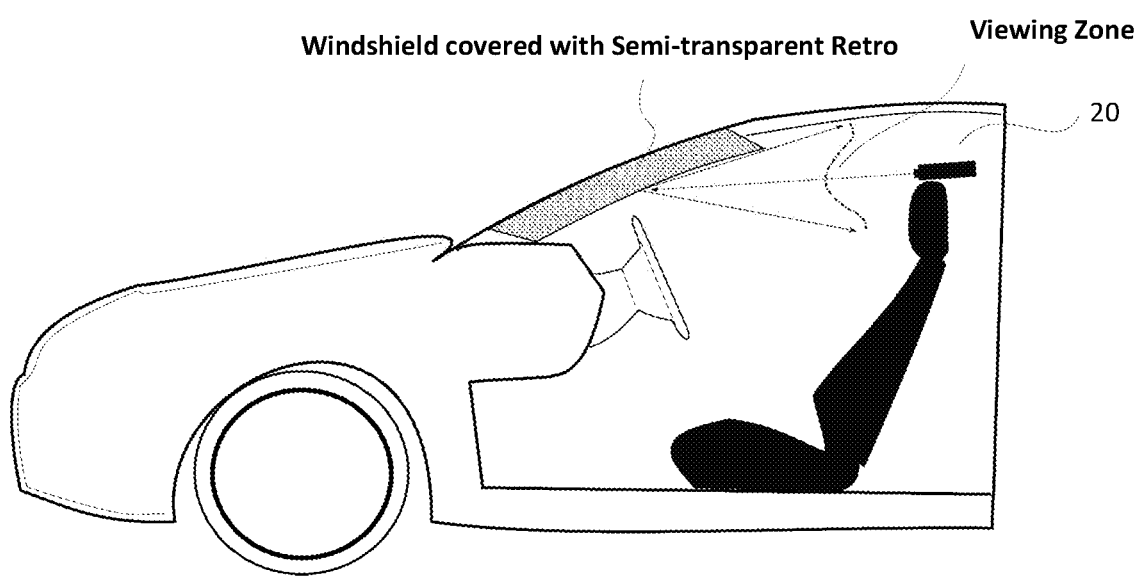
FIG. 9 demonstrates the use of the passive screen having a semi-transparent retroreflective layer as head up display (HUD) screen.

According to the projection display system, the passive screen (11) having a plurality of retroreflective cells (15) together with the screen substrate (13) is a restructurable medium which can be tightly fitted over a solid object so as to tightly conform to the surface contour of the object in a locally reshaped manner. In a more specific manner, the polymer-based passive screen (11) can for instance be worn on a mannequin as a garment-shaped projection display layer so that a plurality of different virtual garments can be generated on the passive screen (11) by the projector unit (20). This situation is demonstrated in FIG. 6. Integration of the head-mountable device (12) with inertial sensors gives the ability to change the projected content as the user moves around the mannequin. Therefore, said head-mountable device (12) has inertial sensors to track head movements and change the projected content accordingly.

Likewise, transparent glasses in museum display cases may have semi-transparent retroreflective layers (23) so that visitors wearing a head-mountable device (12) can view projected virtual content and related information on the glass surface of the display cases. The passive screen (11) will function as a transparent glass for others but as a projection screen for a visitor wearing the head-mountable device (12).

The digital content can be still images or video, which is either overlaid on top of the object or projected on a nearby surface. The digital content can be customized for different people based on language preferences, age, etc.

According to a further embodiment, the passive screen (11) can be integrated to a hand-wearable screen unit (22) for instance in the form of a hand glove with a screen area onto which the planarly constructed passive screen (11) with the semi-transparent retroreflective layer (23) is fitted. This is particularly advantageous in combined use with the head-mountable device (12) allowing the user to view any desired visual content on the allocated passive screen (11) in an accurately scaled manner in spite of the fact that the screen area dynamically changes its position depending on the user's hand motions. The image capturing device (14) within the head-mountable device (12) is used to perform real-time hand tracking using near IR active imaging and perform projection mapping. Transparency of the passive screen (11) can be preferably substantially reduced by increasing the duty cycle of the retroreflective cells (15) for this particular application.

The semi-transparent retroreflective layer (23) can also be used as a head up display (HUD) in the form of a virtual windshield screen in a car. A fixed projector unit (20) placed above the driving seat is used to display navigational or other data on the transparent passive screen (11) having the semi-transparent retroreflective layer (23). The other side of the windshield can be optionally also retroreflective to enhance on road visibility of road safety.

Figure 10:
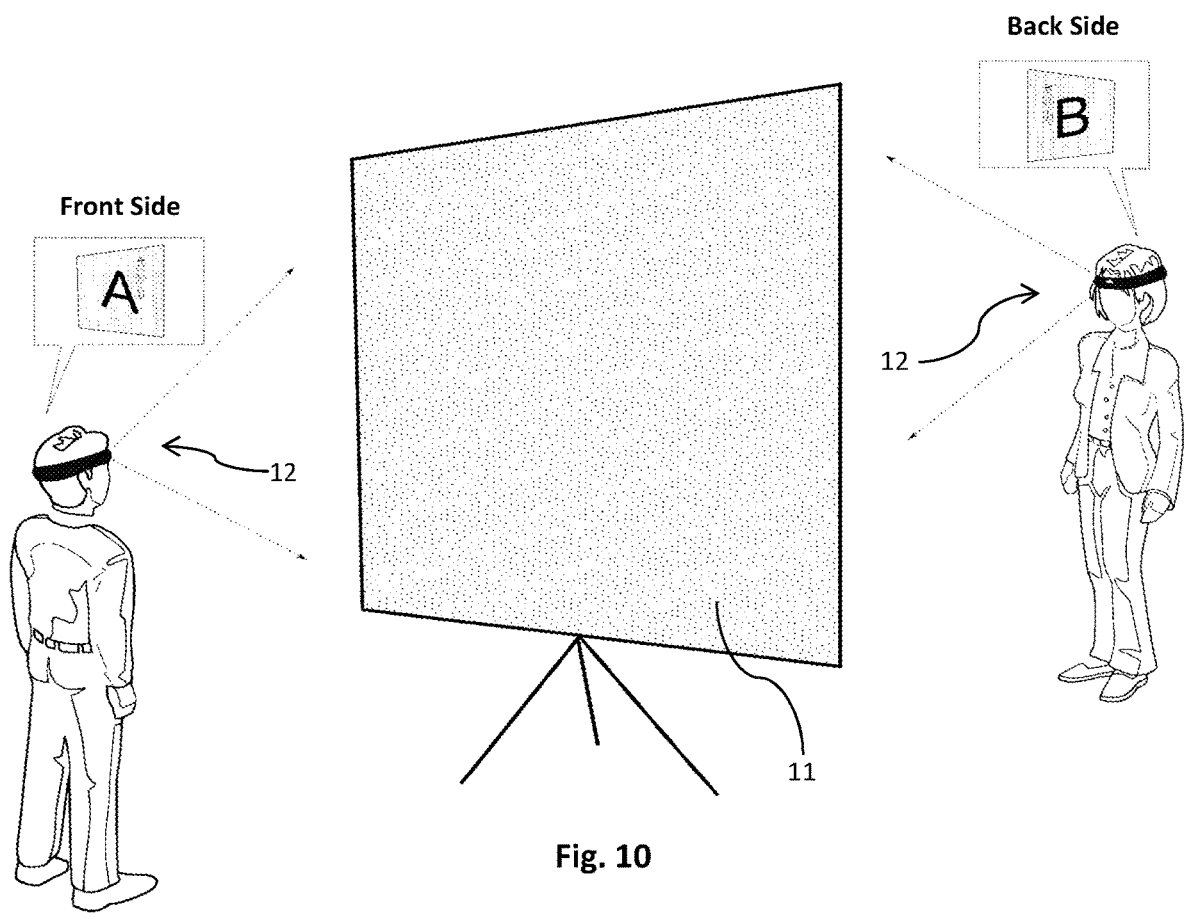
FIG. 10 demonstrates the application of a passive screen in the form of a bidirectional semi-transparent retroreflective layer.
Figure 11:
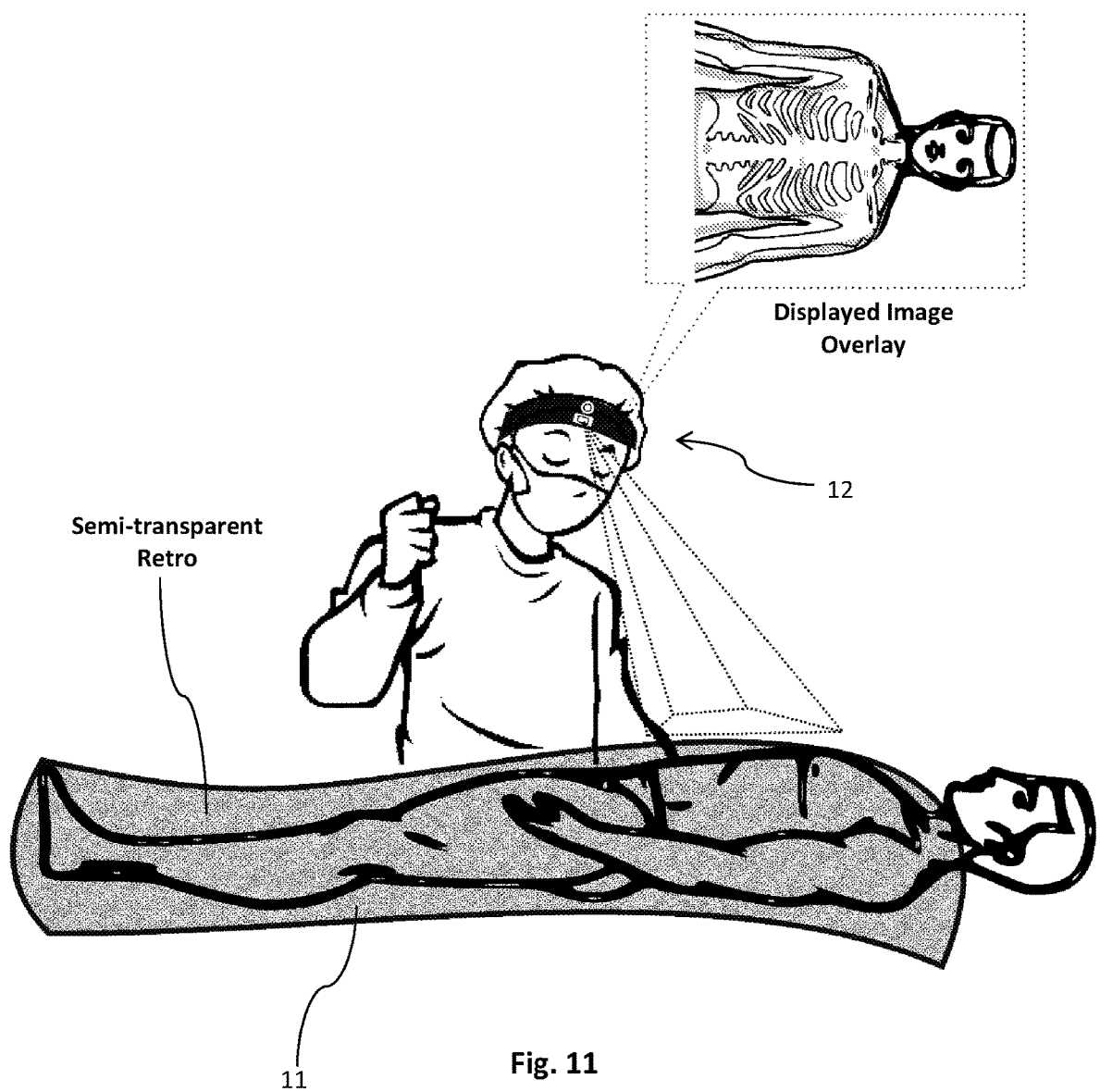
FIG. 11 demonstrates the application of the head-mountable device with the passive screen having the semi-transparent retroreflective layer according to another embodiment, where a patient can be covered with semi-transparent retroreflective layer.

The passive screen (11) with the semi-transparent retroreflective layer (23) having retroreflective cells (15) made of hemi-spherically coated randomly-oriented glass microspheres instead of transparent microspheres placed on the microspheres reflective coating and adhesive layer can be used to create a bi-directional semi-transparent retroreflective layer (23) as shown in FIG. 10. This is particularly advantageous in that two persons with respective head-mountable devices (12) on different sides of the semi-transparent retroreflective layer (23) can view separate visual contents while at the same time viewing the scene at the other side of the passive screen (11) through the semi-transparent retroreflective layer (23). It is possible to absorb the transmitted portion of the laser light from the projector units (20) at an intermediate layer of the passive screen (11). Narrowband notch coatings matching the laser wavelengths can be used in between a stack of retroreflective layers to absorb the laser light.

Further, a patient can be covered with the passive screen (11) having the semi-transparent retroreflective layer (23), and a medical doctor can advantageously perform medical examination by projecting real-time test data (X-rays, CT Scan etc.) directly on human body by means of the head-mountable device (12) comprising the projector unit (20) and the image capturing device (14).

According to the projection display system, surface form irregularities of a solid object onto which a restructurable passive screen (11) will be placed in immediate contact with the surface contour thereof can be sensed by means of a structured-light 3D scanner projecting fringe patterns. The projector unit (20) is typically a laser projector with three visible lasers (RGB) and one near IR laser, the latter used to project fringe patterns on physical objects, thereby performing as a projection beam scanner to measure the three-dimensional shape of the object using projected light patterns. An auxiliary camera (21) as an IR camera with a perspective position captures distorted beams reflected from the object. Therefore, deformations in the projected fringes are analyzed to compute 3D geometry (angular orientation of the projection surface and perspective information of physical objects) for object reconstruction purposes. Use of the projector unit (20) as a structured-light 3D scanner is particularly advantageous in projection applications on certain objects such as furniture, in which case the application serves to the purpose of fabric selection on the furniture. The advantage originates from the fact that certain objects may generally have principal surface areas in substantially different angular orientations, typically as in the case of a sofa with back and seat surfaces. Therefore, the projector unit (20) together with the auxiliary camera (21) will be able to accurately determine angular orientation of both surfaces as in the sofa example.

In the case of a head-mountable device (25), the latter can be conventionally capable of establishing a remote network connection to connect to a remote server for reaching a database of images or image sequences for use in the reconstruction work of the specific object.

The projection surface, i.e. the passive screen (1) can be preferably used as a passive interactive medium. The user can use the projection surface of the passive screen (11) similar to a touch screen using gestures, which are recognized by the image capturing device (14) through image processing. Therefore, hand and finger gestures and touch points on the passive screen (11) are detected by said image capturing device (14), whereby hand and fingers of the users act as an input device for the processing unit in cooperation with the projection unit (20) so that the projected content can be interactively changed in response to the inputs in the form of hand and finger gestures and touch points by the user. Alternatively, a transparent touch screen layer can be added on top of the passive screen (11) in which case the passive screen is combined with an active layer such as a conventional resistive or capacitive layer. The application provides that the input by the user is directly sensed by a control unit in connection with the touch screen layer on top of the passive screen (11) and remotely communicated to the projection unit (20) or the head-mountable device (12) to enhance interaction between the projected content and the user feedback. This is especially advantageous in enhancing accuracy of the user input compared to the configuration where user input is detected only by said image capturing device (14).

Additionally, a haptic interface layer can be added on top of the passive screen (11) to give the feel of the surface pattern being projected on the surface. As an exemplary embodiment, for instance in the case of a semi-transparent retroreflective layer (23) in the form of a garment-shaped projection display layer, the additional haptic interface layer on top of the passive screen (11) can recreate the sense of touching to the fabric by applying forces and vibrations.

In an alternative embodiment, the image capturing device (14) reads and validates information written on a passive screen (11) in the form of a QR code or other code in response to which the projector unit (20) displays content specifically designed for the particular situation. This is especially useful in security applications where a user with a certain authentication level accesses a plurality authentication terminals where a QR code or other code is projected on a passive screen (11) of the authentication terminal by his projector unit (20) and the image capturing device (14) of the authentication terminal reads and validates information in response to which the projector unit (20) projects relevant content.

In the case of a hand-wearable screen unit (22) in combined use with the head-mountable device (12), it is further possible that the image capturing device (14) reads information on real objects (such as QR code) and the user is requested to validate certain information via finger pointing or finger touch on the passive screen (11) of said hand-wearable screen unit (22). More particularly, the image capturing device (14) captures a machine readable code on a real object and the projector unit (20) projects the relevant information in association with the machine readable code. This is for instance useful for logistics applications where the user needs to pick up the correct box with the help of the passive screen (11). Likewise, in the case of a hand-wearable screen unit (22) in combined use with the head-mountable device (12), the projector unit (20) can be adapted to be automatically turned off to save power when it cannot see a retroreflective surface, i.e., the hand-wearable screen unit (22) as it only projects on the allocated screen area and when the hand-wearable screen unit (22) is turned upside down or moved outside the field-of-view, it is turned off.

As a further embodiment, in the case of a bi-directional semi-transparent retroreflective layer (23), the image capturing device (14) and the projector unit (20) cooperates such that if the image capturing device (14) detects a person on the other side of the bi-directional semi-transparent retroreflective layer (23), the corresponding projector unit

(20) pixels are turned off in order not to illuminate or blind the person with the projector light.

In a nutshell, the projection display system proposes a projection display system comprising an image capturing device (14), a projector unit (20) and a passive screen (11).

In one embodiment, said passive screen (11) is formed as a projection display effecting displaying of at least one image projected thereon and comprising a retroreflective layer (23) having a plurality of micro-patterned retroreflective cells (15) or a retroreflective layer (23) in the form of painted retroreflective surface. The projection display system, thanks to the retroreflective layer (23) having a plurality of micro-patterned retroreflective cells (15) or a retroreflective layer (23) in the form of painted retroreflective surface, provides an enhanced optical gain compared to a lambertian scatterer, which is basically more efficiently operable with less laser power particularly advantageous for head-mountable applications.

The head-mountable applications using a head-mountable device (12) are otherwise advantageous in that they basically provide privacy such that only the wearer of the head-mountable device (12) can clearly see the visual content projected onto the passive screen (11) in a certain angle only allowing viewing by the wearer of the device while providing optical gain and high brightness.

In a further embodiment, said passive screen (11) is placeable on a surface of an object in the manner that said image capturing device (14) in optical communication with said passive screen (11) identifies physical boundaries of said passive screen (11) and the projector unit (20) projects at least one image scaled to fit to the passive screen (11) within the boundaries thereof.

In a further embodiment, said retroreflective layer (23) comprising a plurality of retroreflective cells (15) or in the form of painted retroreflective surface is a semi-transparent layer outside the areas of said retroreflective cells (15) or outside the areas of surface portions with retroreflective paint, which has retroreflective microspheres embedded in the paint. Retroreflective paint can be transparent or in different colors.

In a further embodiment, said passive screen (11) comprises a polymer-based screen substrate (13) in the form of a substantially restructurable medium placeable on a solid object in a manner to be tightly fitted over the object so as to tightly conform to the surface contour of said object in immediate contact therewith in a locally reshaped manner. In a further embodiment, said image capturing device (14) identifies physical boundaries of said passive screen (11) by real-time perspective capture and projection mapping in the manner that images are projected on the surface of the passive screen (11) covering the object.

In a further embodiment, the image capturing device (14) and the projector unit (20) are combined to form a position-adjustable device in the form of a table-top device, a ground-standing device, a wall-mounted device or a suspended device.

In a further embodiment, the image capturing device (14) and the projector unit (20) are incorporated into a head-mountable device (12).

In a further embodiment, said head-mountable device (12) effectuates real-time perspective capture, projection mapping and real-time reconstruction of the object in the manner that at least one projected image is scaled to fit to the passive screen (11) irrespective of the changing distance and/or viewing angle of the head-mountable device (12) relative to the passive screen (11). In a further embodiment, said projector unit (20) projects at least one image to dynamically cover the calculated projection zone by boundary-based modification within the boundaries of the passive screen (11) placed on the object. In a further embodiment, said image capturing device (14) comprises a high-resolution camera and the projector unit (20) comprises a high-resolution pico-projector.

In a further embodiment, the retroreflective cells (15) of the semi-transparent retroreflective layer (23) are structured in the form of a micro-patterned retroreflective surface. In a further embodiment, the retroreflective layer (23) comprises retroreflective cells (15) of microspheres coated on a screen substrate (13) of the passive screen (11).

In a further embodiment, the retroreflective layer (23) in the form of painted retroreflective surface comprises retroreflective paint on a screen substrate (13) of the passive screen (11). In a further embodiment, the retroreflective layer (23) comprises surface portions with retroreflective paint mixed with retroreflective microspheres on the screen substrate (13) of the passive screen (11).

In a further embodiment, the retroreflective cells (15) are made of hemi-spherically coated glass microspheres spread in a randomly-oriented manner over an adhesive layer on the screen substrate (13).

In a further embodiment, the adhesive layer is a pressure-sensitive or radiation curable (UV) adhesive/resin.

In a further embodiment, the retroreflective cells (15) are made of transparent microspheres tightly placed on a microspheres reflective coating (18) and pressure sensitive or radiation curable (UV) adhesive/resin on the screen substrate (13).

In a further embodiment, the microspheres reflective coating's (18) thickness is approximately in the range of 75 to 125 nm.

In a further embodiment, the microspheres reflective coating (18) is a metallic and preferably Aluminum or Nickel film. In a further embodiment, microspheres' size is in the range of 10 μm to 150 μm whereby the retro-reflection cone angle emanating from a single microsphere is optimized. In a further embodiment, microspheres have a certain size in the manner that the retroreflective cells (15) are made sufficiently small to prevent granular viewing from a viewing distance of at least 25 cm.

In a further embodiment, the retroreflective cells' (15) pitch is smaller than 1 mm and is preferably at least 100 μm.

In a further embodiment, the retroreflective cells' (15) pattern has a pitch period of 250 μm to 2 mm with a fill factor of 10% to 50%. In a further embodiment, the retroreflective cells' (15) distribution pattern is in the form of evenly distributed, linearly aligned square, hexagonally disposed, dithered, vertical/horizontal strips or randomly distributed patches. In a further embodiment, the retroreflective cells' (15) shape is in the form of circular or square-shaped patch portions.

In a further embodiment, said passive screen (11) comprises a semi-transparent vertical diffusive layer (24) placed on top of said semi-transparent retroreflective layer (23).

In a further embodiment, the semi-transparent vertical diffusive layer (24) comprises vertical diffusive cells (16) in the form of cylindrical lenses, each vertical diffusive cell (16) corresponding in size to the surface area of a respective retroreflective cell (15). In a further embodiment, the passive screen (11) comprises cylindrical lens micro strips (17) to form a vertically diffused only screen.

In a further embodiment, the cylindrical lens micro strips' (17) cylindrical lenses (19) are hemi-spherically coated with a reflective coating (18) so as to retro-reflect light in one direction and scatter light in another direction.

In a further embodiment, the cylindrical lenses (19) are fiber elements.

In a further embodiment, the reflective coating (18) material is aluminum, silver or nickel.

In a further embodiment, the projector unit (20) comprises a near IR laser to project fringe patterns on an object and an auxiliary camera (21) in the form of an IR camera to capture distorted beams reflected from the object whereby deformations in the projected fringes are analyzed to compute 3D geometry of the object. In a further embodiment, the passive screen (11) is integrated to a hand-wearable screen unit (22) with a screen area onto which the planarly constructed passive screen (11) with the semi-transparent retroreflective layer (23) is fitted. In a further embodiment, the projector unit (20) is a battery-operated laser scanning projector.

In a further embodiment, said head-mountable device (12) comprises inertial sensors so as to track head movements in the manner that content projected by the projector unit (20) is changed to be scaled to fit to the passive screen (11). In a further embodiment, hand and finger gestures and touch points on the passive screen (11) are detected by said image capturing device (14) through image processing, whereby the projected content is interactively changed in response to the inputs in the form of hand and finger gestures and touch points.

In a further embodiment, a transparent touch screen layer is added on top of the passive screen (11).

In a further embodiment, a haptic interface layer is added on top of the passive screen (11).

In a further embodiment, the image capturing device (14) and the projector unit (20) are remotely independently operational in the manner that the image capturing device (14) reads and validates information written on a passive screen (11) in the form of a machine-readable code in response to which the projector unit (20) displays the relevant content. In a further embodiment, the image capturing device (14) reads machine-readable codes on real objects and the passive screen (11) presents information as projected by the projector unit (20) on the hand-wearable screen unit (22). In a further embodiment, the projector unit (20) is adapted to be automatically turned off when the hand-wearable screen unit (22) is turned sideways or upside down or moved outside the field-of-view of the image capturing device (14). In a further embodiment, the image capturing device (14) and the projector unit (20) cooperates such that if the image capturing device (14) detects a person on the other side of a bi-directional semi-transparent retroreflective layer (23), the corresponding pixels in the projector unit (20) are turned off.

In a further embodiment, the mage capturing device (14) is an infrared (IR) camera (i.e. near IR, mid-wave IR, long wave IR, or thermal camera).

In a further embodiment, the projector unit (20) is adapted to effect displaying of at least one image captured by said image capturing device (14) in optical communication with a human or non-human circulatory system and said passive screen (11) is formed as a retroreflective layer (23) in the form of painted retroreflective surface, whereby the projector unit (20) projects at least one image scaled to fit onto body parts of a human or non-human on which the passive screen (11) is disposed such that circulatory system veins are displayed.

Therefore, the present invention ensures that a nurse can easily locate veins in patients and blood donors by mapping them onto the skin thanks to the projector unit (20) of the invention. The nurse or paramedic wearing the head-mountable device (12) of the invention can easily locate the veins as captured by said image capturing device (14) and displayed on the passive screen (11) as a retroreflective layer (23) in the form of painted retroreflective surface disposed for instance on the arm of a patient.

In a further embodiment, the projector unit (20) is adapted to effect displaying of at least one image captured by said image capturing device (14) in optical communication with a circuit board and said passive screen (11) is formed as a retroreflective layer (23) in the form of painted retroreflective surface, whereby the projector unit (20) projects at least one image scaled to fit onto the circuit board on which the passive screen (11) is disposed such that thermal map inspection of hot spots is effected. Therefore, the present invention ensures that a hot spot on a circuit board can be extremely practically identified in the course of the operation of the circuit, i.e. for instance during different stages of the operation involving different power modes under different electrical loads.

In a further embodiment, the projector unit (20) is adapted to effect displaying of at least one image in optical communication with a garment-shaped passive screen (11) wearable on a mannequin, whereby the projector unit (20) projects at least one image scaled to fit onto the passive screen (11).

In a further embodiment, the projector unit (20) is adapted to effect displaying of at least one image in optical communication with a passive screen (11) placeable on a museum display case, whereby the projector unit (20) projects at least one image scaled to fit onto the passive screen (11).

In a further embodiment, the projector unit (20) is adapted to effect displaying of at least one image in optical communication with a passive screen (11) disposable on a windshield of a car, whereby the projector unit (20) projects at least one image scaled to fit onto the passive screen (11) in the form of a windshield head up display.

In a further embodiment, the projector unit (20) is adapted to effect displaying of at least one image in optical communication with a passive screen (11) disposable as a patient examination or surgery table cover, whereby the projector unit (20) projects at least one image scaled to fit onto the passive screen (11).

In a further embodiment, a passive screen (11) comprising a semi-transparent retroreflective layer (23) having retroreflective cells (15) is proposed, said semi-transparent retroreflective layer (23) being an at least partially see-through layer in the manner that images of a projector unit (20) projecting images on a first side of the semi-transparent retroreflective layer (23) at least partially overlap with the physical view of an object on which the semi-transparent retroreflective layer (23) is placeable. In a further embodiment, the retroreflective cells (15) have microspheres coated on a screen substrate (13) of the passive screen (11), said microspheres being either hemi-spherically coated glass microspheres spread in a randomly-oriented manner over an adhesive layer on the screen substrate (13) or transparent microspheres tightly placed on a microspheres reflective coating and adhesive/resin on the screen substrate (13).

In a further embodiment, said semi-transparent retroreflective layer (23) is a bi-directional semi-transparent retroreflective layer (23) comprising hemi-spherically coated glass microspheres spread in a randomly-oriented manner over an adhesive layer on the screen substrate (13).

In a further embodiment, a method for manufacturing a passive screen (11) having retroreflective cells (15) is proposed, said method comprising the steps of applying pressure sensitive or radiation curable (UV) adhesive/resin to a screen substrate (13) using a surface pattern having surface openings for receiving the pressure sensitive or radiation curable (UV) adhesive/resin, applying a microspheres reflective coating on the surface openings containing pressure sensitive or radiation curable (UV) adhesive/resin and tightly placing transparent microspheres on said microspheres reflective coating.

In a further embodiment, use of a passive screen (11) comprising a semi-transparent retroreflective layer (23) as a garment-shaped projection display layer is proposed In a further embodiment, use of a passive screen (11) comprising a semi-transparent retroreflective layer (23) as a display case glass layer is proposed.

In a further embodiment, use of a passive screen (11) comprising a semi-transparent retroreflective layer (23) as a windshield head up display of a car.

In a further embodiment, use of a passive screen (11) comprising a semi-transparent retroreflective layer (23) as a patient examination or surgery table cover is proposed.

In a further embodiment, use of a passive screen (11) comprising a semi-transparent retroreflective layer (23) in the form of painted retroreflective surface as a circulatory system examination cover is proposed. In a further embodiment, use of a passive screen (11) having a retroreflective layer (23) with retroreflective paint on a screen substrate (13) as a water-proof pool basin construction element is proposed. A plurality of such construction elements can advantageously cover the pool basin and a swimmer training during consecutive hours and wearing the head-mountable device (12) of the invention can enjoy any visual content being projected on the basin surface. The head-mountable device (12) as well as the construction elements can be made water-proof in a conventional manner.

In a further embodiment, use of a passive screen (11) comprising a semi-transparent retroreflective layer (23) as a circuit board thermal examination cover is proposed. It is to be noted that both for the circulatory system examination cover and the circuit board thermal examination cover, the passive screen (11) should be advantageously semi-transparent in which a plurality of discrete portions in the form of retroreflectively painted surface portions are present.

In a further embodiment, an alternative projection display system is proposed, which comprises an image capturing device (14) and a projector unit (20) wherein the image capturing device (14) and the projector unit (20) are incorporated into a head-mountable device (12), the image capturing device (14) is an IR camera and said projector unit (20) is adapted to effect displaying of at least one image captured by said image capturing device (14) whereby the projector unit (20) projects at least one image scaled to fit onto a surface portion to effectuate thermal map inspection of hot spots.

In a further embodiment, the alternative projection display system's projector unit (20) is adapted to effect displaying of at least one image captured by said image capturing device (14) in optical communication with a human or non-human circulatory system, whereby the projector unit (20) projects at least one image scaled to fit onto body parts of a human or non-human such that circulatory system veins are displayed.

In a further embodiment, the alternative projection display system's projector unit (20) is adapted to effect displaying of at least one image captured by said image capturing device (14) in optical communication with a circuit board, whereby the projector unit (20) projects at least one image scaled to fit onto the circuit board such that thermal map inspection of hot spots is effected.

Therefore, the present invention ensures that a nurse can easily locate veins in patients and blood donors by mapping them onto the skin thanks to the projector unit (20) of the invention. The nurse or paramedic wearing the head-mountable device (12) of the invention can easily locate the veins as captured by said image capturing device (14) as directly projected for instance on the arm of a patient.

Further, according to the present invention ensures a hot spot on a circuit board can be identified as directly projected on the circuit board in the course of the operation of the circuit during different stages of the operation. In a further embodiment, a further alternative projection display system is proposed, which comprises a projection display system comprising an image capturing device (14) and a projector unit (20) wherein the image capturing device (14) and the projector unit (20) are incorporated into a head-mountable device (12), the image capturing device (14) is a terahertz camera and said projector unit (20) is adapted to effect displaying of at least one image captured by said image capturing device (14) whereby the projector unit (20) projects at least one image scaled to fit onto a surface portion to effectuate internal inspection of an object. This is particularly advantageous in security inspections by which the content of a packet can be externally identified.

The cases where X-ray scanning fails to correctly detect plastic explosives is especially important as projected content by the terahertz camera on a surface portion of a suspected packet can directly identify the inner contents of the package. According to the invention, the image capturing device (14) can be selected to be operable in different wavelengths of the electromagnetic spectrum.

The invention claimed is:

1. A projection display system comprising:
an image capturing device;
a projector unit configured to project a visible image and a fringe pattern; and
a passive screen formed as a projection display effecting display of at least one image projected thereon and comprising a semi-transparent retroreflective layer comprising a plurality of micro-patterned retroreflective cells, a painted retroreflective surface, or a combination thereof,
wherein the semi-transparent retroreflective layer comprises microspheres coated on a screen substrate of the passive screen structured in a micro-patterned retroreflective surface, a pattern of the retroreflective cells having a pitch period of 250 µm to 2 mm with a fill factor of 10% to 50%,
wherein said passive screen is placeable on a surface of an object having irregularities in a manner that said image capturing device is in optical communication with said passive screen and detects said fringe pattern to identify physical boundaries and a three-dimensional shape of said passive screen based on said irregularities, and said projector unit projects at least one visible image in accordance with said irregularities and scaled to fit to the passive screen within the physical boundaries thereof.

2. The projection display system as set forth in claim 1, wherein the painted retroreflective surface is a semi-transparent layer outside areas of said retroreflective cells or outside areas of surface portions with retroreflective paint.

3. The projection display system as set forth in claim 1, wherein said passive screen comprises a polymer-based screen substrate comprising a substantially restructurable medium placeable on a solid object in a manner to be tightly fitted over the object so as to tightly conform to a surface contour of the irregularities in the surface of said object in immediate contact therewith in a locally reshaped manner.

4. The projection display system as set forth in claim 1, wherein the image capturing device and the projector unit are combined as a position-adjustable device, the position-adjustable device being a table-top device, a ground-standing device, a wall-mounted device or a suspended device.

5. The projection display system as set forth in claim 4, wherein the projector unit is adapted to effect display of at least one image in optical communication with the passive screen, the passive screen disposable on a windshield of a car as a windshield head up display, and the projector unit is configured to project at least one image scaled to fit on the windshield head up display.

6. The projection display system as set forth in claim 1, wherein the image capturing device and the projector unit are incorporated into a head-mountable device.

7. The projection display system as set forth in claim 6, wherein the passive screen is integrated into a hand-wearable screen unit with a screen area onto which the passive screen with the retroreflective layer is fitted, wherein the passive screen is planarly constructed and the retroreflective layer is semi-transparent.

8. The projection display system as set forth in claim 6, wherein the image capturing device is an infrared (IR) camera, and the projector unit is configured to project the fringe pattern with IR light.

9. The projection display system as set forth in claim 6, wherein the projector unit is adapted to effect display of at least one image in optical communication with the passive screen, the passive screen disposable as a patient examination or surgery table cover, and the projector unit is configured to project at least one image in accordance with said irregularities of said three-dimensional shape of said patient examination or surgery table cover and scaled to fit onto the passive screen.

10. The projection display system as set forth in claim 6, wherein said head-mountable device is configured to effectuate real-time perspective capture, projection mapping and real-time reconstruction of the object so that at least one projected image is scaled to fit to the passive screen irrespective of changing distance and/or viewing angle of the head-mountable device relative to the passive screen.

11. The projection display system as set forth in claim 1, wherein the microspheres are transparent microspheres placed on a microspheres reflective coating and pressure sensitive or radiation curable (UV) adhesive/resin on the screen substrate.

12. The projection display system as set forth in claim 1, wherein a size of the microspheres is in a range of 10 µm to 150 µm to optimize a retro-reflection cone angle emanating from each of the microspheres.

13. The projection display system as set forth in claim 1, wherein a distribution pattern of the retroreflective cells is evenly distributed, linearly aligned square, hexagonally disposed, dithered, vertical/horizontal strips or randomly distributed patches.

14. The projection display system as set forth in claim 1, wherein said passive screen comprises a semi-transparent vertical diffusive layer placed on top of said retroreflective layer.

15. The projection display system as set forth in claim 1, wherein the passive screen comprises cylindrical lens micro strips arranged to form a vertically diffused only screen.

16. The projection display system as set forth in claim 1, wherein the image capturing device is configured to detect hand and finger gestures and touch points on the passive screen with image processing, and wherein the image capturing device is configured to interactively change content projected by the image capturing device in response to inputs in a form of hand and finger gestures and touch points.

17. The projection display system as set forth in claim 16, wherein the passive screen comprises a transparent touch screen layer included on top of the passive screen.

18. A projection display system comprising:
   a projector unit configured to separately project a visible image and a fringe pattern;
   a passive screen comprising a semi-transparent retroreflective layer comprising a plurality of micro-patterned retroreflective cells a painted retroreflective surface, or a combination thereof;
   wherein the semi-transparent retroreflective layer comprises microspheres coated on a screen substrate of the passive screen structured in a micro-patterned retroreflective surface, a pattern of the retroreflective cells having a pitch period of 250 µm to 2 mm with a fill factor of 10% to 50%,
   wherein said semi-transparent retroreflective layer is an at least partially transparent layer such that images projected by the projector unit on a first side of the semi-transparent retroreflective layer at least partially overlap with a physical view of an object on which the semi-transparent retroreflective layer is placeable, the object including irregularities causing a three dimensional shape of the passive screen; and
   an image capturing device configured to detect the fringe pattern to identify physical boundaries and the three-dimensional shape of said passive screen based on said irregularities, and said projector unit configured to project a visible image in accordance with said irregularities, the visible image scaled to fit to the three dimensional shape of the passive screen within the physical boundaries thereof.

19. The projection display system as set forth in claim 18, wherein said microspheres being either hemi-spherically coated glass microspheres spread in a randomly-oriented manner over an adhesive layer on the screen substrate or transparent microspheres tightly placed on a microspheres reflective coating and adhesive/resin on the screen substrate.

20. A projection display system comprising:
   a passive screen comprising a semi-transparent retroreflective layer including a plurality of micro-patterned retroreflective cells, a painted retroreflective surface, or a combination thereof;
   wherein said semi-transparent retroreflective layer is an at least partially transparent layer structured in a micro-patterned retroreflective surface comprising microspheres forming a pattern of the retroreflective cells having a pitch period of 250 µm to 2 mm with a fill factor of 10% to 50% such that images projected by a projector unit on a first side of the semi-transparent retroreflective layer at least partially overlap with a physical view of an object on which the semi-transparent retroreflective layer is placeable.

\* \* \* \* \*